United States Patent [19]

Shiga et al.

[11] Patent Number: 4,661,519

[45] Date of Patent: Apr. 28, 1987

[54] METHOD FOR DERMATOLOGICAL APPLICATION

[75] Inventors: Takuo Shiga, Shizuoka; Kazuo Nabeta, Yokosuka; Hiroyuki Nakano, Hayama; Toshimitsu Suzuki, Yokohama, all of Japan

[73] Assignee: Pola Chemical Industries Inc., Shizuoka, Japan

[21] Appl. No.: 745,832

[22] Filed: Jun. 18, 1985

Related U.S. Application Data

[63] Continuation of Ser. No. 484,270, Apr. 12, 1983, abandoned.

[51] Int. Cl.$^4$ ............................................. A61K 31/225
[52] U.S. Cl. ..................................... 514/547; 514/859
[58] Field of Search .............................. 514/547, 558

[56] References Cited

U.S. PATENT DOCUMENTS

| | | | |
|---|---|---|---|
| 3,928,420 | 12/1975 | Fang | 200/475 P |
| 4,052,513 | 10/1977 | Kaplan | 424/310 |
| 4,261,982 | 4/1981 | Luedders et al. | 424/181 |
| 4,386,104 | 5/1983 | Nazzaro-Porro | 514/558 |

OTHER PUBLICATIONS

Chemical Abstracts 98: 146354p (1983).
Chemical Abstracts 71: 61931s (1969).

*Primary Examiner*—Leonard Schenkman

[57] ABSTRACT

Composition for dermatological application to be used for freckles, liver-spots, and acnes containing as an active constituent 0.1 to 40 wt % of a dicarboxylic acid ester, having 7 to 13 carbon atoms as activated constituent and represented by the general formula of

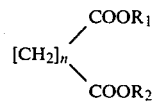

wherein
n=5–11
$R_1$=ethyl, isopropyl, glyceryl, or H,
$R_2$=ethyl, isopropyl, glyceryl or H,
and wherein $R_1$ and $R_2$ together are diethyl, diisopropyl, and diglyceryl, and H and ethyl, H and isopropyl, H and glyceryl.

4 Claims, No Drawings

METHOD FOR DERMATOLOGICAL APPLICATION

This application is a continuation of application Ser. No. 484,270, filed Apr. 12, 1983, abandoned.

BACKGROUND OF THE INVENTION

1. Field of the Invention

The present invention concerns a composition for dermatological application effective for use in treatment of liver-spots, freckles, pigmentations, acnes, etc. and is based on the novel pharmacological discovery that certain dicarboxylic acid esters exhibit properties useful in such treatment.

2. Description of the Prior Art

It is known that dicarboxylic acids, their reductive derivatives and salts thereof are pharmacologically effective in treatment of chromatopathia such as liver-spots, freckles, etc. When these dicarboxylic acids are to be used as a pharmacological composition for dermatological application, they are found to be extremely inferior in their solubility in fats and oils. Therefore, there are considerable difficulties in preparing them into various dosage forms. Moreover, they tend to be instable as they become crystallized and separated with the passage of time. Accordingly, the tendency is that there are problems for dicarboxylic acids to manifest their original pharmacological actions, and for obtaining preparations of satisfactory properties. Although their salts improve the water dispersing property and therefore makes pharmaceutical preparation easier, they tend to cause irritation to the skin if applied carelessly depending on the degree of neutralization because of their property as a soap. This may cause problems in safety, and discomfort in use. It may at times inhibit the above mentioned effects. There are approximately same problems as regards the reductive derivatives of dicarboxylic acids. These problems and difficulties have not yet been solved.

SUMMARY OF THE INVENTION

The present invention aims to offer a composition for dermatological application which is free of the above mentioned problems and defects and used for treatment and prevention of liver-spots, freckles, pigmentations, acnes, etc. and in sum it is characterized in that it contains as an active constituent 0.1–40 wt.%, or more preferably 3–20 wt.% of dicarboxylic acid ester having 7 to 13 carbon atoms as an active constituent represented by the general formula of

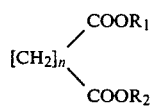

In the general formula,
n=5–11
$R_1$=ethyl, isopropyl, glyceryl,
$R_2$=ethyl, isopropyl, glyceryl, or H,
and wherein $R_1$ and $R_2$ together are diethyl, diisopropyl, and diglyceryl, and H and ethyl, H and isopropyl, and H and glyceryl.

DETAILED DESCRIPTION OF THE INVENTION

A composition of this invention is characterized in that it contains as an active constituent 0.1 to 40 wt% of a dicarboxylic acid ester, having 7 to 13 carbon atoms as the active constituent and represented by the general formula as set forth above. Specific examples of dicarboxylic acid esters used in above composition are; monoethyl pimelate, diethyl pimelate, monoisopropyl pimelate, diisopropyl pimelate, monoglyceryl pimelate, diglyceryl pimelate, monoethyl suberate, diethyl suberate, monoisopropyl suberate, monoglycerol suberate, diglyceryl suberate, monoethyl azelate, monoisopropyl azelate, diisopropyl azelate, monoglyceryl azelate, diglyceryl azelate, monoethyl sebacate, diethyl sebacate, monoisopropyl sebacate, diisopropyl sebacate, monoglyceryl sebacate, diglyceryl sebacate, monoethyl 1,10-decamethylene dicarboxylate, diethyl 1,10-decamethylene dicarboxylate, monoisopropyl 1,10-decamethylene dicarboxylate, diisopropyl 1,10-decamethylene dicarboxylate, monoglyceryl 1,10-decamethylene dicarboxylate, diglycerol 1,10-decamethylene dicarboxylate, monoethyl 1,11-undecamethylene dicarboxylate, diethyl 1,11-undecamethylene dicarboxylate, monoisopropyl 1,11-undecamethylene dicarboxylate, diisopropyl 1,11-undecamethylene dicarboxylate, monoglyceryl 1,11-undecamethylene dicarboxylate, diglyceryl 1,11-undecamethylene dicarboxylate, etc.

One, two or more than two of these esters are used, and more preferably monoglyceryl suberate, diglyceryl suberate, monoglyceryl azelate, diglyceryl azelate, monoglyceryl pimelate, diglyceryl pimelate, monoglyceryl sebacate, diglyceryl sebacate, etc. are used.

Esters of dicarboxylic acids according to this invention are restricted to the following specific one from the point of therapeutic effects of dicarboxylic acids. Whenever n is 4 or less or 12 or more in the above general formula, it is not possible to obtain the aimed effective composition for dermatological application. If the content prepared is less than 0.1 wt.%, sufficient effect is not to be expected. If it exceeds 40 wt.%, the effect was not observed to have enhanced.

More specifically, it has been found that when:
(i) the content is less than 0.1 wt.%: Adequate efficacy cannot be expected.
(ii) the content is in excess of 40.0 wt.%: Improvement is hardly recognized.
(iii) the content is out of the range of 3.0 to 20.0 wt.% (preferable range):
  (1) 0.1 to less than 3.0 wt.%: Efficacy is recognized, but cannot be deemed as significant.
  (2) more than 20.0 wt.% and less than 40 wt.%: The system tends to become unstable, and the preparation tends to cause discomfort when applied.

There are various manners for preparing esters of dicarboxylic acids related to present invention. For example, by using none solvent or a polar solvent such as acetone etc. depending on circumstances according to a customary manner, one or more dicarboxylic acids of carbon number 7–13 are mixed with at least one equivalent of one or more alcohols of ethanol, isopropanol, glycerine etc., then a catalyst of such as sulfuric acid etc. is added to the mixture and the mixture is subjected to the reaction under the room or enhanced temperature. After finishing the reaction, the esters of dicarboxylic acids are separately refined with distillation or the use of a column chromatography. Besides, it is also possible to prepare glyceryl esters of dicarboxylic acids with the addition reaction of the fatty acids and glycidols.

Synthetic examples of esters of dicarboxylic acids using for present invention are as follows.

Synthetic Example 1: Monoglyceryl Azelate Ester

Azelaic acid 158 g, glycerine 250 g, acetone 500 ml and concentrated sulfuric acid 2 ml are mixed and reacted by stirring them for 8-10 hours. After the reaction, benzene 500 ml is added to the reaction product in order to separate unreacted glycerine. This procedure is repeated at several times.

Then, 5% sodium bicarbonate water solution is added to the benzene layer until stopping to generate carbonic acid gas, then the water layer is separated. This water layer is made to weak acid with 5% Hcl solution, then extracted with ethyl acetate at three times. After distilling the solvent, the reaction product is applied to silicagel column chromatography in order to separately prepare monoglyceryl azelate ester 80 g with ethyl ether, thereafter chloroform methanol (8:2)

White crystal m.p. 42°-43° C.
Elementary analysis

| C (%) | | H (%) | |
|---|---|---|---|
| Measurement | Calculation | Measurement | Calculation |
| 55.03 | 54.96 | 8.97 | 8.40 |

NMR (CDCl$_3$ + CD$_3$OD)
δ value  1.1-1.7   —CH$_2$— (10H)
         2.1-2.3   —CH$_2$CO— (4H)
         3.4-4.1   —OCH$_2$—,
                   |
                   —CH—O— (5H)

Synthetic Example 2: Diglyceryl Azelate Ester

Azelaic acid 158 g and glycerine 500 g are mixed with acetone 700 ml. Then conc. sulfuric acid 2 ml is added to the mixture and the mixture is subjected to the reaction by stirring it under the room temperature for 4 hours.

Then, after distilling acetone away for finishing the reaction, generated water is removed from the reaction product by sucking for several hours at 50°-60° C. by using an aspirator. After that, n-butanol 500 ml is added to the residue and after the solvent is distilled away, the residue is separately refined by using silicagel column chromatography (chloroform:methanol=9:1) in order to prepare diglyceryl azelate ester 250 g.

White crystal m.p. 35°-36° C.
Elementary analysis

| C (%) | | H (%) | |
|---|---|---|---|
| Measurement | Calculation | Measurement | Calculation |
| 53.39 | 53.57 | 8.35 | 8.33 |

NMR (CDCl$_3$ + CD$_3$OD)

δ value
1.1-1.8   —CH$_2$— (10 H)
2.2-2.4   —CH$_2$CO— (4 H)
3.2-4.2   —OCH$_2$—, —CH—O— (10 H)

Synthetic Example 3: Diglyceryl Sebacate Ester

Sebacic acid 172 g and glycerine 500 g is mixed with acetone 700 ml. Then, conc. sulfuric acid 2 ml is added to the mixture and the mixture is subjected to reaction by stirring it under the room temperature for 4 hours. Then, after distilling acetone away for finishing the reaction, generated water is removed from the reaction product by sucking for several hours at 50°-60° C. by using an aspirator. After that, n-butanol 500 ml is added to the residue and after distilling solvent away, the residue is separatedly refined by using silicagel column chromatography (chloroform:methanol=9:1) in order to prepare diglyceryl sebacate about 270 g.

White crystal m.p. 37°-38° C.
Elementary analysis

| C (%) | | H (%) | |
|---|---|---|---|
| Measurement | Calculation | Measurement | Calculation |
| 54.92 | 54.86 | 8.66 | 8.57 |

NMR (CDcl$_3$ + CD$_3$OD)
δ  1.1-1.7   —CH$_2$— (2H)
   2.2-2.4   —CH$_2$CO— (4H)

3.2-4.2
                        |
             —CCH$_2$—, —CHO— (10H)

The significant point in the present invention is that some of dicarboxylic acid esters become liquified at room temperature and for this unique feature they are used as the oily base in cosmetic preparations. However, there has so far been practically no example of the practical use as an effective constituent of a composition aiming at pharmacological effects in treating/preventing liver-spots, freckles, pigmentations, acnes as in the present invention. Only an extremely limited number of examples has been objectively proved of their efficacy and recognized as the effective constituent for topical application. Although there are exceptions such as various Vitmain C, it is true that the therapeutic effects in its original meaning have not been fully demonstrated including the problems of forming the composition into various forms. In the case of the present invention, dicarboxylic acid esters are stably present in the preparation, and when they are applied to the skin, they are restored to dicarboxylic acids by the enzyme activity in the skin, and manifest remarkable therapeutic effects for the various symptoms of abnormal skin, and achieve the desired purposes.

The result of experiments in which we have confirmed that various dicarboxylic acid esters according to the present invention become restored to dicarboxylic acids which are free active constituent when they are absorbed transcutaneously and the ester bond becomes broken is shown in Table I(A). The experiment was conducted by using p-nitrophenyl acetate and by incubating the skin homogenate processed with citric acid-phosphoric acid buffer solution and various dicarboxylic acid esters on the shaved back of a guinea pig, and the time required for conversion to dicarboxylic acid and the ratio of conversion by esterase activity in the skin of a guinea pig. The compatibility with various oils and fats are also shown in Table 1 in the column B along with the examples of dicarboxylic acids.

TABLE 1

| | (A) Monoester of dicarboxylic acid, dicarboxylic acid | | (B) compatability with oils/fats | |
|---|---|---|---|---|
| | diester → monoester (2 hrs.) | monoester → dicarboxylic acid (3 hrs.) | squalen | olive oil |
| Sample | | | | |
| diglyceryl | 85 | 9 | ⊚ | ○ |

TABLE 1-continued

| | (A) Monoester of dicarboxylic acid, dicarboxylic acid | | (B) compatability with oils/fats | |
|---|---|---|---|---|
| | diester → monoester | monoester → dicarboxylic acid | | |
| Sample | (2 hrs.) | (3 hrs.) | squalen | olive oil |
| sebacate | | | | |
| diglyceryl azelate | 71 | 8 | ○ | ○ |
| diethyl sebacata | 100 | 45 | ○ | ○ |
| diethyl azelate | 95 | 38 | ⊚ | ⊚ |
| diisopropyl azelate | 95 | 41 | ⊚ | ⊚ |
| monoethyl sebacate | — | 35 | ○ | ○ |
| monoethyl azelate | — | 34 | ○ | ○ |
| isopropyl sebacate | 93 | 41 | ⊚ | ⊚ |
| sebacic acid | — | — | X | X |
| azelic acid | — | — | X | X |

*Evaluation Standards for Compatability with Fats and Oils.
⊚: Easily soluble
○ : Soluble
X: Hard to dissolve (or insoluble)

As is clear from Table 1, esters of dicarboxylic acids were restored to dicarboxylic acids within the skin. Specifically, monoglyceryl esters of dicarboxylic acids were found to be restored to dicarboxylic acids which showed pharmacodynamic effects on a skin or on the process of subcutaneous absorption in a short time as compared with other esters. The therapeutic effects thereof for liver-spots, freckles, pigmentation acnes, etc. are remarkably demonstrated when they are subcutaneously absorbed. We also conducted the experiment for confirming the same restoration effect in respect of the human skin, and obtained substantially similar results.

The results of the experiments demonstrating the superiority of the composition for dermatological application containing dicarboxylic acid esters in accordance with the present invention over the conventional products are shown in Table II. The method used in application was as follows. Sixty females ranging from 18 to 40 in age having different symptoms of abnormality of the skin were divided into four groups, and they were told to apply the skin coating composition described in the examples 1 to 4 once a day for 6 months to their face, and to observe the healing conditions of the diseased part on which the cream was applied.

The preparation according to the example 1 was given to those suffering from "liver-spots", that according to the example 2 "freckles" and the example 3 and 4 to "acnes". The degree of improvements as shown in Table II were graded as follows, and the average grades were shown.
1: No change
2: Seems to have somewhat improved
3: Somewhat improved
4: Clearly improved
5: Substantially healed The invention product was compared to the conventional products by following the half-face comparison method. The overall evaluation is shown as the results in the table.

TABLE II

| | Degree of Improvement | | | Comparison with the conventional products |
|---|---|---|---|---|
| Sample | After 2 months | After 4 months | After 6 months | |
| Example 1 | 2.3 | 3.5 | 4.7 | Invention product is superior |
| Example 2 | 2.0 | 3.5 | 4.5 | Invention product is superior. |
| Example 3 | 2.1 | 3.9 | 4.8 | Invention product is extremely superior. |
| Example 4 | 1.2 | 2.3 | 3.3 | Invention product is somewhat superior |

Table II clearly shows the superiority of the present invention product over the conventional products. Besides, for examples 1 and 2, the same treatment was conducted to the ladies of "dark skinned" symptoms and almost equivalent improved effects to "liver-spots" and "freckles" were obtained with it.

The following comparative examples supplement Table II.

TABLE II (SUPPLEMENT)

| | Improvement | | | |
|---|---|---|---|---|
| SAMPLE | after 2 mo. | after 4 mo. | after 6 mo. | comparison with commercial product |
| a | 1.0 | 1.5 | 1.5 | — |
| b | 1.5 | 2.3 | 3.3 | — |
| c | 2.1 | 3.9 | 4.9 | — |

Comparative Example a: contains 0.01 wt.% of diglyceryl azelate of Example 1 (cream for dematological uses) with the balance being substituted by increasing the water content.

Comparative Example b: contains 0.1 wt.% of diglyceryl azelate of Example 1 (cream) with the balance being substituted by increasing the water content.

Comparative Example c: contains 50.0% of monoglyceryl sebacate of Example 3 with the balance being decreased with the water content.

The preparation of Comparative Example a for dermatological uses containing 0.01 wt.% of diglyceryl azelate hardly shows any improvement after 2 to 6 months. As for comparative Example b which contains 0.1 wt.% of said substance, a slight improvement is observed after 6 months and its apparent efficacy is recognized. The comparative Example C contains as much as 50 wt.% of monoglyceryl sebacate, but improvement on the efficacy is hardly visible when compared with Example 3 which contains 15.0 wt.% of said substance.

We had further conducted the experiment to demonstrate that the composition for dermatological application in accordance with the present invention is stable as a preparation and superior in its safety; the result of the experiment using the comparison products A and B by respectively substituting dicarboxylic acid ester (diglyceryl azelate) and dicarboxylic acid salts (neutralized product of sodium azelate, neutralized by 100%) and the skin cream of the example 1 are shown in Table III. The stability test was carried out by leaving the above mentioned specimens for 20 days at the constant temperatures of 20° C. and 40° C. respectively, and the safety test was carried out by following the animal (rabbit) skin irritation test.

TABLE III

| Specimen | Stability | | Safety |
|---|---|---|---|
| Present Invention | 20° C.: | No change | No irritation |
| | 40° C.: | No change | |
| Comparison Example A | 20° C.: | Crystallized & separated after 2 days | strong irritating |
| | 40° C.: | Instantly separated | |
| Comparison Example B | 20° C.: | No change | Strongly irritating (pH value becomes changed toward alkali side and irritates the skin) |
| | 40° C.: | Slight change | |
| Comparative Example X | 20° C.: | fine crystals appear | not irritant |
| | 40° | shows no change | |

Comparative Example X: Contains 30.0 wt.% of diglyceryl azelate of Example 1 to be described below with the balance being decreased with the water content.

Table III shows that the present invention product has no instability as a preparation which characterizes the comparison A, and the irritation to the skin which the comparison compound B showed and which arose from compounding of dicarboxylic acid salts was resolved. The present invention composition of the comparison B may be used in the various forms such as cream, lotion, emulsion, powder, ointment and gel by concurrently using the moulding agent, the solution agent, the complement agent, and following the usual method of preparation.

As discussed hereinabove, the present invention concerns the composition for skin application to be used for liver-spots, freckles pigmentation, acnes, etc. And by giving a solution to the problems in the course of preparation, it lets the pharmacological effects arising from dicarboxylic acid in topical application manifest themselves and offers stable and safe preparation. The preparation for dermatological preparation in accordance with the present invention may be applied to cosmetics in addition to the topical medicine because of the advantages they have.

The examples of the composition in accordance with the present invention are now discussed below. The content ratio is given in wt. %.

Example 1: Skin Cream

| | | |
|---|---|---|
| A | cetanol | 3.0 |
| | spermaceti | 4.0 |
| | stearic acid | 1.0 |
| | squalene | 7.0 |
| | diglyceryl azelate | 10.0 |
| | P.O.E.(20) sorbitan monooleate | 2.5 |
| | sorbitan monostearate | 2.0 |
| | P.O.E. cholesterol | 0.5 |
| B | propylene glycol | 7.0 |
| | water to make up the total to | 100.0 |

A and B are respectively heated to 75° C., and B is added to A while stirring. Following addition, the mixture is cooled to 30° C. and the aimed substance for skin cream is obtained.

Example 2: Skin Cream

| | | |
|---|---|---|
| A | cetanol | 3.0 |
| | spermaceti | 3.0 |
| | stearic acid | 1.0 |
| | octyldodecyl myristate | 8.0 |
| | diglyceryl sebacate | 10.0 |
| | P.O.E.(20) sorbitan monooleate | 2.0 |
| | monoglyceride stearate | 2.0 |
| | P.O.E. cholesterol | 1.0 |
| B | propylene glycol | 7.0 |
| | water to make up the total to | 100.0 |

The skin cream is obtained in the same way as the above example 1.

Example 3: Ointment for Skin

| | | |
|---|---|---|
| A | vaseline | 4.5 |
| | lanolin | 1.0 |
| | spermaceti | 2.0 |
| | monoglyceryl sebacate | 15.0 |
| | squalane | 7.5 |
| | P.O.E.(20) sorbitan monooleate | 2.0 |
| | sorbitan monooleate | 3.0 |
| B | water to make up the total to | 100.0 |

After heating A and B respectively to 70° C., B is added to A while stirring A. Following addition, the mixture is cooled to 35° C., and the aimed substance for ointment for the skin is obtained.

Example 4: Skin Lotion

| | | |
|---|---|---|
| A | polyoxy ethylene oleyl ether | 3.0 |
| | salt of sodium lauryl sulfate | 0.5 |
| | sodium chloride | 0.1 |
| | water | 1.0 |
| B | diethyl azelate | 2.0 |
| | monoglyceryl azelate | 3.0 |
| | polyoxy ethylene hardened castor oil | 1.0 |
| C | water to make up the total to | 100.0 |

A is dissolved at 70° C. and added to B. C is added to dilute the mixture which is then cooled to 30° C. The aimed substance for the skin lotion is obtained.

What we claim is:

1. A dermatological treatment method for freckles, liver-spots, pigmentations and acne, primarily to reduce pigmentation, which comprises the step of applying a composition, to the affected locales of the skin, containing from about 3.0 to 20 wt.% of a dicarboxylic acid ester having 7 to 13 carbon atoms and represented by the formula:

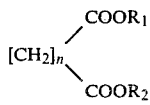

wherein
n=5-11
$R_1$ is glyceryl and
$R_2$ is glyceryl or H
in a pharmaceutically acceptable topical carrier.

2. The method according to claim 1, wherein the dicarboxylic acid ester is selected from the group consisting of monoglyceryl pimelate; diglyceryl pimelate;

monoglyceryl suberate; diglyceryl suberate; monoglyceryl azelate; diglyceryl azelate; monoglyceryl-1,9-nonamethylene dicarboxylate; diglyceryl-1,9-nonamethylene dicarboxylate; monoglyceryl-1,10-decamethylene dicarboxylate; diglyceryl-1,10-decamethylene dicarboxylate; monoglyceryl-1,11-undecamethylene dicarboxylate; diglyceryl-1,11-undecamethylene decarboxylate.

3. The method according to claim 1 wherein the dicarboxylic acid ester is selected from the group consisting of monoglyceryl suberate; diglyceryl suberate; monoglyceryl azelate; diglyceryl azelate; monoglyceryl-1,9-nonamethylene dicarboxylate; diglyceryl-1,9-nonamethylene dicarboxylate; monoglyceryl sebactate; diglyceryl sebacate.

4. The method according to claim 1 wherein the dicarboxylic acid ester is selected from the group consisting of monoglyceryl azelate; diglyceryl azelate; monoglyceryl sebacate; diglyceryl sebacate.

* * * * *